United States Patent
Anselmann et al.

(10) Patent No.: US 6,743,285 B1
(45) Date of Patent: *Jun. 1, 2004

(54) PIGMENT MIXTURE COMPRISING BIOCl PIGMENTS

(75) Inventors: Ralf Anselmann, Ramsen (DE); Uta Hillgärtner, Darmstadt (DE); Sabine Schoen, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/069,669

(22) PCT Filed: Aug. 16, 2000

(86) PCT No.: PCT/EP00/07947
§ 371 (c)(1),
(2), (4) Date: Feb. 28, 2002

(87) PCT Pub. No.: WO01/16235
PCT Pub. Date: Mar. 8, 2001

(30) Foreign Application Priority Data

Sep. 1, 2000 (DE) .......................... 199 41 607

(51) Int. Cl.⁷ ............................... C04B 14/00
(52) U.S. Cl. .................. 106/415; 106/417; 106/418; 106/479
(58) Field of Search ............................... 106/417, 418, 106/479

(56) References Cited

U.S. PATENT DOCUMENTS

| | | | | | |
|---|---|---|---|---|---|
| 3,980,491 | A | * | 9/1976 | Eberts ........................ | 106/291 |
| 4,116,628 | A | * | 9/1978 | Hesse et al. ................. | 427/154 |
| 6,267,810 | B1 | * | 7/2001 | Pfaff ........................... | 106/415 |
| 6,334,893 | B1 | * | 1/2002 | Pfaff et al. .................. | 106/442 |
| 6,372,036 | B1 | * | 4/2002 | Pfaff et al. .................. | 106/443 |
| 6,517,628 | B1 | * | 2/2003 | Pfaff et al. .................. | 106/417 |

FOREIGN PATENT DOCUMENTS

| | | | |
|---|---|---|---|
| DE | 4432225 | * | 3/1996 |
| DE | 44 32 225 A | | 3/1996 |
| DE | 0960911 | * | 12/1999 |
| EP | 0 960 911 A | | 12/1999 |

* cited by examiner

*Primary Examiner*—C. Melissa Koslow
*Assistant Examiner*—Shalie Manlove
(74) *Attorney, Agent, or Firm*—Millen, White, Zelano & Branigan, P.C.

(57) ABSTRACT

The present invention relates to pigment mixtures in the form of a dispersion or powder, consisting of at least two components, where component A comprises coated or uncoated BiOCl pigments in the form of a powder or dispersion, and component B comprises pearlescent pigments, platelet-shaped, needle-shaped or spherical colorants and/or fillers, and to the use thereof in paints, coatings, printing inks, plastics, powder coatings, plastic films, for the finishing of seed and in particular in cosmetic formulations.

15 Claims, No Drawings

PIGMENT MIXTURE COMPRISING BIOCl PIGMENTS

The present invention relates to pigment mixtures in dispersion or in the form of a powder, consisting of at least two components, where component A comprises BiOCl pigments in the form of a powder or dispersion, and component B comprises pearlescent pigments, platelet-shaped, needle-shaped or spherical colorants and/or fillers, and to the use thereof in paints, coatings, printing inks, plastics, powder coatings, plastic films, for the finishing of seed and in particular in cosmetic formulations.

Since BiOCl pigments have a high refractive index (n=2.15) and a pearl-like or metallic silver lustre, they are employed in paints, coatings, plastics and in particular in cosmetic products. In addition to the metallic silver lustre or pearl lustre, the consumer of decorative products expects ever greater functionality and thus makes ever greater demands on the appearance. The BiOCl pigments disclosed in German Patent 10 03 377, U.S. Pat. No. 2,975,053, DE 24 11 966, EP 0 496 686 B1 and DE 43 05 280 A1 have the disadvantage that they either do not have variable hiding power, have inadequate metallic lustre, do not have an absorption colour, do not have an interference colour and/or do not have a light diffusing effect.

The object of the present invention was to provide a pigment mixture comprising BiOCl pigments which is distinguished by high, variable hiding power or variable transparency and/or increased metallic lustre, can be incorporated well into the respective application system and is stable therein, and in which a visible BiOCl/colorant or BiOCl/filler separation in the system is substantially excluded. Furthermore, the abrasion, application and skin feel in cosmetic materials should be improved compared with the products on the market.

Surprisingly, a pigment mixture has now been found which has none of the above-mentioned disadvantages. The pigment mixture according to the invention consists of at least two components, where component A comprises coated or uncoated BiOCl pigments in the form of a powder or dispersion, and component B comprises pearlescent pigments, in particular based on mica, $SiO_2$, glass, $Al_2O_3$, $TiO_2$, graphite or polymer platelets, platelet-shaped, needle-shaped or spherical colorants and/or fillers.

The admixing of component B with the BiOCl pigments enables increased metallic lustre to be imparted to the application systems, the colour effect is increased, and novel colour effects are achieved. At the same time, the pigment mixture is distinguished by its variable, i.e. controllable, hiding power from virtually invisible to strongly hiding. In addition, the functionality of the end product is improved. Formulations comprising the pigment mixture according to the invention have an excellent skin feel, high skin affinity, long-wear properties, variable hiding power, if desired metallic lustre, good ease of incorporation into the end product, and comparatively high light stability.

The invention thus relates to a pigment mixture consisting of at least two components, where component A comprises coated or uncoated BiOCl pigments in the form of a powder or dispersion, and component B comprises pearlescent pigments, platelet-shaped, needle-shaped or spherical colorants and/or fillers.

The invention likewise relates to the use of the pigment mixture according to the invention in paints, coatings, printing inks, including printing inks for security printing, plastics, plastic films, powder coatings, for the finishing of seed and in particular in cosmetic formulations.

The BiOCl pigments in the form of a powder can be mixed with component B in any ratio. The ratio of component A to component B is preferably from 1:90 to 90:1, particularly preferably from 1:50 to 50:1 and in particular from 1:20 to 20:1.

BiOCl pigments are commercially available and are offered, for example, by Merck KGaA, Germany, under the trade names Biron®, Bital®, Bicrona®, Mibiron® and Nailsyn®. Owing to the diverse production possibilities, BiOCl pigments having different optical properties, from matt to glossy and from transparent to hiding, are obtainable. The size of the individual particles is 1–100 µm, preferably 1–40 µm and in particular 2–35 µm. The BiOCl pigments employed may be coated or uncoated. In the case of the coated BiOCl pigments, the coating preferably consists of metal oxides, such as, for example, $TiO_2$, $TiO_2$ sub-oxides, $Fe_2O_3$ and mixtures thereof or organic or inorganic colorants of natural and synthetic origin. Preferred pigment mixtures comprise BiOCl pigments which are coated with $Fe_2O_3$, Carmine Red, Berlin Blue or Chromium Oxide Green.

As a dispersion, the BiOCl is preferably initially in the form of a paste with nitrocellulose lacquers or castor oil and is subsequently mixed with component B. The pigment mixture according to the invention in the form of a powder or dispersion is distinguished by good dispersibility, pH stability, heat stability and storage stability in the end product.

Besides pastes with castor oil and nitrocellulose lacquers, dispersions in water, polar and nonpolar oils, polyols, hydrophilic and hydrophobic solvents, volatile or non-volatile, are likewise suitable.

Preferred pigment mixtures comprise, in particular, one or more pearlescent pigments as colorant (=component B) in addition to the BiOCl pigments (=component A). The pearlescent pigments used are, in particular, pigments based on platelet-shaped, transparent or semi-transparent substrates made from, for example, phyllosilicates, such as, for example, synthetic or natural mica, talc, sericite, kaolin, or other silicate materials, which are coated with coloured or colourless metal oxides, such as, for example, $TiO_2$, titanium sub-oxides, titanium oxynitrides, pseudobrookite, $Fe_2O_3$, $Fe_3O_4$, FeOOH, $SnO_2$, $Cr_2O_3$, ZnO, CuO, NiO and other metal oxides, alone or in the form of a mixture in a single layer or in successive layers.

Pearlescent pigments are disclosed, for example, in the German patents and patent applications 14 67 468, 19 59 998, 20 09 566, 22 14 454, 22 15 191, 22 44 298, 23 13 331, 25 22 572, 31 37 808, 31 37 809, 31 51 343, 31 51 354, 31 51 355, 32 11 602, 32 35 017, 38 42 330 and 44 45 394 and are commercially available, for example under the trade names Colorona®, Timiron®, Dichrona®, Microna® and Soloron®, from Merck KGaA, Darmstadt, Germany.

Particularly preferred pigment preparations comprise $TiO_2$, $Fe_2O_3$, $TiO_2$ sub-oxides, $TiO_2/Fe_2O_3$, $Fe_3O_4$, FeOOH or FeOOH/$TiO_2$ mica pigments. Preference is furthermore given to $TiO_2$, graphite, $Fe_2O_3$, $SiO_2$ or $Al_2O_3$ platelets coated with $TiO_2$ and/or $Fe_2O_3$.

Further suitable platelet-shaped pigments are, in particular, pearlescent pigments based on $SiO_2$ platelets, $Al_2O_3$, graphite, polymer or $TiO_2$ platelets or glass platelets which are covered with one or more metal-oxide layers (one, two, three, five or seven).

Also suitable as component B are the multilayered pigments disclosed, for example, in DE-A 196 18 563, DE-A 196 18 566, DE-A 196 18 569, DE-A 197 07 805, DE-A 197 07 806 and DE-A 197 46 067. These are based on a platelet-shaped, transparent, coloured or colourless matrix consisting of mica (synthetic or natural), $SiO_2$ platelets, glass platelets, $Al_2O_3$ platelets, $TiO_2$ platelets or polymer platelets and generally have a thickness of between 0.3 and 5 μm, in particular between 0.4 and 2.0 μm. The extension in the two other dimensions is usually between 1 and 250 μm, preferably between 2 and 100 μm, and in particular between 5 and 40 μm. The multilayered pigments consist of the matrix (substrate) coated with metal oxides (at least two). The coating of the substrate platelets, such as, for example, mica, $SiO_2$ platelets, glass platelets or $Al_2O_3$ platelets, with a plurality of layers is carried out in such a way that a layer structure consisting of alternating high- and low-refractive-index layers is formed. The multilayered pigments preferably comprise 2, 3, 4, 5, 6 or 7 layers, in particular 3, 4 or 5 layers. Suitable high-refractive-index metal oxides are, for example, titanium dioxide, zirconium oxide, zinc oxide, iron oxides, iron-titanium oxides (iron titanates) and/or chromium oxide, in particular $TiO_2$ and/or $Fe_2O_3$. The low-refractive-index metal oxides used are $SiO_2$ and $Al_2O_3$. However, $MgF_2$ or an organic polymer (for example acrylate) can also be employed for this purpose. The substrate platelets can be coated, for example, as described in WO 93/08237 (wet-chemical coating) or DE-A 196 14 637 (CVD process).

Preferred multilayered pigments have the following structure:

substrate+$Fe_2O_3$ layer+$SiO_2$ layer+$Fe_2O_3$ layer
substrate+$Fe_2O_3$ layer+$SiO_2$ layer+$TiO_2$ layer
substrate+$TiO_2$ layer+$SiO_2$ layer+$Fe_2O_3$ layer
substrate+$TiO_2$ layer+$SiO_2$ layer+$TiO_2$/$Fe_2O_3$ layer
substrate+$TiO_2$/$Fe_2O_3$ layer+$SiO_2$ layer+$TiO_2$/$Fe_2O_3$ layer
substrate+$TiO_2$ layer+$SiO_2$ layer+$Cr_2O_3$ layer
substrate+$TiO_2$ layer+$SiO_2$ layer+$TiO_2$ layer Instead of the outer metal-oxide layer, it is also possible to use a semi-transparent layer of a metal. Suitable metals for this purpose are, for example, Cr, Ti, Mo, W, Al, Cu, Ag, Au or Ni.

In order to achieve specific colour effects, finely divided particles in the nanometre size range may additionally be incorporated into the high- or low-refractive-index layers. Suitable for this purpose have proven to be, for example, finely divided $TiO_2$ or finely divided carbon (carbon black) having particle sizes in the range 10–250 nm. The light-scattering properties of particles of this type enable the lustre and hiding power to be modified in a targeted manner.

The pearlescent or multilayered pigments in component B may also be provided with a protective layer in order to improve the light, weathering and chemical stability or in order to increase the compatibility in various media. Suitable subsequent coatings or subsequent treatments are the processes described, for example, in DE 22 15 191, DE 31 51 354, DE 32 35 017 or DE 33 34 598. The additionally applied substances make up only from about 0.1 to 5% by weight, preferably from 0.5 to 3.0% by weight, of the multilayered pigment.

Suitable as component B for the pigment mixture according to the invention are all platelet-shaped, needle-shaped and spherical colorants or fillers known to the person skilled in the art which have a particle size of from 0.001 to 20 μm, preferably from 0.01 to 5 μm. The pigment mixtures according to the invention preferably comprise absorption pigments as colorants and platelet-shaped or spherical powders as fillers.

Particularly suitable are platelet-shaped substrates which, on the basis of mica, are coated with an organic and/or inorganic dye of synthetic or natural origin.

The spherical colorants include, in particular, $TiO_2$, $BaSO_4$, coloured or coated $SiO_2$, $CaSO_4$, iron oxides, chromium oxides, carbon black, organic and inorganic coloured pigments of synthetic or natural origin, such as, for example, carmine, Berlin Blue, anthraquinone pigments, quinacridone pigments, diketopyrrolopyrrole pigments, phthalocyanine pigments, azo pigments and isoindoline pigments. Of the spherical colorants, $SiO_2$ is preferred. The $SiO_2$ beads may be coated or uncoated. The $SiO_2$ beads are preferably coated with $TiO_2$, $Fe_2O_3$, FeOOH, $Fe_3O_4$, Berlin Blue or chromium oxide green in one or more layers. The spherical particles, for example made of $SiO_2$, preferably have a $TiO_2/Fe_2O_3$, $SiO_2$, $TiO_2/Fe_2O_3$ coating or a $TiO_2$, $SiO_2$, $TiO_2$ coating.

Of the multicoated $SiO_2$ beads, particular preference is given to those which are coated alternately with 3, 5 or 7 layers of metal oxides of different refractive indices. Spherical $SiO_2$ particles having a particle size of from 1 to 30 μm are commercially available, for example under the trade names Ronasphere® and Micronasphere® from Merck KGaA.

The needle-shaped pigments are preferably ZnO, $Fe_2O_3$, coloured glass fibres, α-FeOOH, organic coloured pigments, such as, for example, azo pigments, β-phthalocyanine Cl Blue 15:3, Cromophtal Yellow 8GN (Ciba-Geigy), Irgalith Blue PD56 (Ciba-Geigy), azomethine copper complex Cl Yellow 129 or Irgazine Yellow 5GT (Ciba-Geigy). Particular preference is given to needle-shaped $Fe_2O_3$.

The addition of a UV stabiliser to the pigment mixture according to the invention is frequently advisable, in amounts of from 0.01–10% by weight, preferably 0.01–5% by weight and in particular 0.01–3% by weight, based on the BiOCl content. Particularly suitable UV stabilisers are those which are commercially available under the name Eusolex® (Merck KGaA), such as, for example, Eusolex® 4360, a 2-hydroxy4-methoxybenzophenone. Also suitable are organic and inorganic light-protection filters in the form of a powder or in dispersion, for example based on micronised $TiO_2$, such as, for example, Eusolex® T-2000 or Eusolex® T-Aqua.

The pigment mixture according to the invention is simple and easy to handle. The pigment mixture can be incorporated into the application system by simple stirring-in in the form of a powder or in the form of a dispersion. Complex grinding and dispersion of the pigments is unnecessary.

The pigment mixture according to the invention can be used for the pigmentation of paints, powder coatings, coatings, printing inks, security printing inks, plastics, artificial pearls and jewellery articles, agricultural sheeting, seed coatings, button pastes and in cosmetic formulations, such as, for example, lipsticks, nail varnishes, cosmetic sticks, powder compacts, make-ups, shampoos, loose powders and gels.

The pigment mixture according to the invention is furthermore suitable for rendering an X-ray catheter tube in which it is incorporated readily visible to the doctor on the X-ray screen. Due to the pigment mixture, the tube remains flexible and smooth.

The concentration of the pigment mixture in the application system to be pigmented is generally between 0.1 and 70% by weight, preferably between 0.1 and 50% by weight and in particular between 1.0 and 20% by weight, based on the total solids content of the system. It is generally dependent on the specific application.

Plastics comprising the pigment mixture according to the invention in amounts of from 0.01 to 50% by weight, preferably from 0.01 to 25% by weight, in particular from 0.1 to 7% by weight, based on the plastic composition, are frequently distinguished by particular metallic lustre.

In the coatings area, the pigment mixture is employed in amounts of from 0.1 to 30% by weight, preferably from 1 to 10% by weight, based on the coating dispersion. The mixing ratio of the BiOCl pigments with component B depends on the desired effect. The BiOCl pigments are preferably employed with component B in a ratio of from 10:1 to 1:10. Compared with finishes comprising only a pearlescent pigment based on mica, finishes comprising the pigment mixture according to the invention have significantly higher metallic lustre.

The pigment mixture according to the invention can also advantageously be employed in decorative and care cosmetics. The high-lustre BiOCl dispersions in combination with component B are preferably employed in pastes, in particular in lipsticks and nail varnishes. Mixtures according to the invention comprising flake-like, irregular BiOCl pigments in the form of a powder are used, in particular, in eye shadow, rouge, cosmetic sticks and make-up powders of all types. In decorative cosmetics, the pigment mixtures according to the invention enable particularly uniform application of the powder to the skin and result in an improvement in the skin feel and in a light diffusing wrinkle hiding effect. In addition, the skin adhesion is improved and cracking during pressing is prevented. Furthermore, the pigment mixture according to the invention in the cosmetic formulation exhibits an improvement in abrasion or application and in distribution, variable hiding power from transparent to hiding and/or a lustre from matt to glossy.

The use concentration and the mixing ratio of BiOCl pigments with component B, in particular organic and inorganic coloured pigments and dyes, of natural or synthetic origin, such as, for example, chromium oxide, ultramarine, coated or uncoated spherical $SiO_2$ or $TiO_2$ pigments, as disclosed, for example, in DE-A 198 42 134, are dependent on the application medium and the effect to be achieved. The mixing of BiOCl pigments in the form of a powder or dispersion with other pigments or dyes can take place in all ratios, the ratio preferably being from 1:10 to 10:1. The use concentration extends from 1% by weight in nail varnish to 70% by weight in powder compacts. In a mixture of BiOCl pigments with spherical fillers, for example $SiO_2$, the concentration can be 0.01–70% by weight in the formulation. The cosmetic products, such as, for example, nail varnishes, lipsticks, powder compacts, shampoos, loose powders and gels, are distinguished by particularly interesting gloss and/or colour effects. In lipsticks and nail varnishes, the pigment mixture is used, in particular, in the form of a dispersion. For use in lipsticks, 70% pigment mixture pastes are preferably used.

Nail varnishes preferably comprise thixotropic, toluene-free, formaldehyde-free nitrocellulose pastes of the pigment mixture. The nitrocellulose pastes generally comprise 40–75% by weight of nitrocellulose and 25–60% by weight of pigment mixture. The metallic silver lustre in nail varnish can be significantly increased with the aid of the pigment mixtures according to the invention compared with conventional nail varnishes. Furthermore, the pigment mixture according to the invention can be employed in bath additives and toothpastes.

In the pigmentation of binder systems, for example for paints and printing inks for gravure printing, offset printing or screen printing, or as precursor for printing inks, for example in the form of highly pigmented pastes, granules, pellets, etc., pigment mixtures consisting of BiOCl pigments with spherical colorants, such as, for example, $TiO_2$, carbon black, chromium oxide, iron oxide and organic "coloured pigments" have proven particularly suitable. The pigment mixture is generally incorporated into the printing ink in amounts of 2–35% by weight, preferably 5–25% by weight and in particular 8–20% by weight. Offset printing inks may comprise the pigment mixture in an amount of up to 40% by weight or more. The precursors for printing inks, for example in the form of granules, pellets, briquettes, etc., comprise up to 95% by weight of the pigment mixture according to the invention in addition to the binder and additives. The mixing ratio of component A to component B is preferably in the range from 1:10 to 10:1. Printing inks comprising the pigment mixture according to the invention exhibit purer hues and can be printed better owing to the good viscosity values.

The invention thus also relates to formulations comprising the pigment mixture according to the invention.

The following examples are intended to illustrate the invention, but without restricting it.

EXAMPLES

Example 1

Long-lasting lipstick comprising 10% of pearlescent pigment and 5% of Biron ® MTU

| Phase | Ingredient | Composition | Manufacturer | % |
|---|---|---|---|---|
| A | Colorona ® Bright Gold | $TiO_2$/$Fe_2O_3$ mica pigment having a particle size of 10–60 μm | (1) | 5.00 |
|  | Colorona ® Bordeaux | $Fe_2O_3$ mica pigment having a particle size of 10–60 μm | (1) | 5.00 |
|  | Biron ® MTU | BiOCl pigment having a particle size of 15 μm | (1) | 5.00 |
| B | Covalip LL 48 | Ozokerite, Candellila Cera, Isostearyl Alcohol, Isopropyl Palmitate, Myristyl Lactate, Cera Alba, Copernicia Cerifera, Quaternium-18 Hectorite, Propylene, Carbonate, Ethylene/VA Copolymer, Propylparaben | (2) | 44.00 |
|  | Dow Corning 556 | Phenyl Trimethicone | (3) | 2.70 |
|  | (–)-α-Bisabolol | Bisabolol | (1) | 0.30 |
| C | Dow Corning 345 | Cyclomethicone | (3) | 28.00 |
|  | Pigment Rouge Covasil W 3801 C, (10% in DC 345) | $Fe_2O_3$, Cyclomethicone | (2) | 10.00 |

Preparation:

Melt all constituents of phase B together and stir until everything has melted. Stir in the pearlescent pigments and the BiOCl pigments of phase A. Slowly add phase C, cool the composition to about 60° C. with stirring, and pour into slimstick containers in two stages. The formulation must be prepared in an explosion-protected apparatus.

Sources of Supply:

(1) Merck KGaA (2) Les Colorants Wackherr (3) Dow Corning

Example 2

Rouge

| Phase | Ingredient | Composition | Manufacturer | % |
|---|---|---|---|---|
| A | Microna ® Matte Red | Fe₂O₃ mica pigment having a particle size of <15 μm | (1) | 21.50 |
| | Microna ® Matte White | TiO₂/ZnO mica pigment having a particle size of <15 μm | (1) | 7.00 |
| | Microna ® Matte Orange | Fe₂O₃ mica pigment having a particle size of <15 μm | (1) | 0.50 |
| | Microna ® Matte Yellow | FeOOH mica pigment having a particle size of <15 μm | (1) | 0.50 |
| | Microna ® Matte Black | Fe₃O₄ mica pigment having a particle size of <15 μm | (1) | 0.50 |
| | Biron ®ESQ | BiOCl pigment | (1) | 5.00 |
| | Micronasphere ® M | Mica/SiO₂ | (1) | 5.00 |
| | Talcum | Talc | (1) | 18.00 |
| | White clay | Kaolin | (1) | 25.00 |
| | Rice starch | Oryza Sativa (Rice Starch) | (1) | 5.00 |
| | Magnesium stearate | Magnesium Stearate | (1) | 2.00 |
| B | Isopropyl myristate | Isopropyl Myristate | (1) | 8.00 |
| | Dow Corning Q2-1403 fluid | Dimethicone, Dimethiconol | (2) | 1.00 |
| | Dow Corning 200 (350 cs) fluid | Dimethicone | (2) | 1.00 |

Preparation:

Combine, pre-mix and sieve (100 μm) the constituents of phase A. Subsequently stir in the binder dropwise. The powders are pressed at 40–50 bar.

Sources of Supply:

(1) Merck KGaA (2) Dow Corning

Example 3

Lipstick comprising 5% of pearlescent pigments and 14.30% of Biron Silver CO

| Phase | Ingredient | Composition | Manufacturer | % |
|---|---|---|---|---|
| A | Biron ® Silver CO | BiOCl pigment in castor oil | (1) | 14.30 |
| | Colorona ® Imperial Red | TiO₂/mica pigment + Cl 73360 (D&C Red #30) having a particle size of 10–60 μm | (1) | 5.00 |
| B | Beeswax | Cera Alba (Beeswax) | (1) | 8.75 |
| | Paracera C 44 | Ceresin, Copernicia Cerifera (Carnauba Wax) | (2) | 5.25 |
| | Adeps Lanae SP | Lanolin | (3) | 3.50 |
| | Isopropyl myristate | Isopropyl Myristate | (1) | 5.60 |
| | Liquid paraffin | Paraffinum Liquidum (Mineral Oil) | (1) | 2.10 |
| | Oxynex ® K liquid | PEG-8, Tocopherol, Ascorbyl Palmitate, Ascorbic Acid, Citric Acid | (1) | 0.05 |
| | Preservative | | | q.s. |
| | Castor oil | Ricinus Communis (Castor Oil) | (3) | 54.45 |
| | Eusolex ® 4360 | Benzophenone-3 | (1) | 1.00 |
| C | Perfume oil | Perfume | | q.s. |

Preparation:

The constituents of phase B are heated to 75° C. and melted. The pigments of phase A are added, and everything is stirred well. The lipstick composition is then stirred for 15 minutes in the casting apparatus heated to 65° C. and perfumed. The homogeneous melt is poured into the casting moulds which have been pre-heated to 55° C. The moulds are subsequently cooled, and the castings are removed cold. After the lipsticks have been heated to room temperature, they are briefly flame treated.

Sources of Supply:

(1) Merck KGaA (2) Paramelt (3) Henry Lamotte (4) Haarmann & Reimer

Example 4

Eye shadow

| Phase | Ingredient | Composition | Manufacturer | % |
|---|---|---|---|---|
| A | Biron ® B 50 | BiOCl pigment having a particle size of 2–35 μm | (1) | 3.00 |
| | Microna ® Matte Black | Fe₃O₄/mica pigment having a particle size of <15 μm | (1) | 0.50 |
| | Ronasphere ® | Silica | (1) | 5.00 |
| | Magnesium stearate | Magnesium Stearate | (1) | 2.50 |
| | White clay | Kaolin | (1) | 5.00 |
| | Hubersorb 600 | Calcium Silicate | (2) | 0.50 |
| | Talcum | Talc | (1) | 15.80 |
| B | Colorona ® Magenta | TiO₂/mica pigment + Cl 75470 (carmine) having a particle size of 10–60 μm | (1) | 55.00 |
| C | Amerchol L-101 | Mineral Oil, Lanolin Alcohol | (3) | 10.70 |
| | Super Hartolan | Lanolin Alcohol | (4) | 1.00 |
| | Ewalin 1751 | Petrolatum | (5) | 1.00 |
| | Preservative | | | q.s. |
| | Perfume oil | | | q.s. |

Preparation:

Combine the constituents of phase A and sieve through 63 μm. Subsequently add phase B, and add the molten phase C dropwise to the powder mixture with vigorous stirring. The powders are pressed at 40–50 bar.

Sources of Supply:

(1) Merck KGaA (2) Huber (3) Amerchol (4) Croda (5) H. E. Wagner

Example 5

Lip powder comprising 30% of pearlescent pigment and 10% of Biron ® fines

| Phase | Ingredient | Composition | Manufacturer | % |
|---|---|---|---|---|
| A | Colorona ® Bordeaux | Fe₂O₃ mica pigment | (1) | 30.00 |
| | Biron ® fines | BiOCl pigment having a particle size of 2–20 μm | (1) | 10.00 |

Lip powder comprising 30% of pearlescent pigment and 10% of Biron ® fines

| Phase | Ingredient | Composition | Manufacturer | % |
|---|---|---|---|---|
| | Talcum | Talc | (1) | 30.00 |
| | Ronasphere ® LDP | Silica with TiO$_2$/Fe$_2$O$_3$ coating | | 10.00 |
| | Magnesium stearate | Magnesium Stearate | (1) | 5.00 |
| B | Isopropyl stearate | Isopropyl Stearate | (2) | 11.20 |
| | Dow Corning 1403 fluid | Dimethicone, Dimethiconol | (3) | 3.80 |
| | Perfume oil | | | q.s. |
| | Preservative | Propylparaben | | q.s. |

Preparation:

Combine and pre-mix the constituents of phase A. Subsequently add the molten phase B dropwise to the powder mixture with stirring. The powders are pressed at 40–50 bar.

Sources of Supply:
(1) Merck KGaA
(2) Henkel KGaA
(3) Dow Corning

Example 6

Creamy eye shadow

| Phase | Ingredient | Composition | Manufacturer | % |
|---|---|---|---|---|
| A | Colorona ® Dark Blue | TiO$_2$ mica pigment with Berlin Blue having a particle size of 10–60 µm | (1) | 10.00 |
| | Timiron ® Supersheen MP-1001 | TiO$_2$ mica pigment having a particle size of 5–25 µm | (1) | 10.00 |
| | Biron ® LF 2000 | BiOCl pigments having a particle size of <20 µm | (1) | 10.00 |
| | Talcum | Talc | (1) | 10.00 |
| B | Crodamol PMP | PEG-2 Myristyl Ether Propionate | (2) | 32.90 |
| | Syncrowachs HGLC | C18–36 Acid Triglyceride | (2) | 10.00 |
| | Syncrowachs HRC | Tribehenin | (2) | 3.00 |
| | Miglyol 812 neutral oil | Caprylic/Capric Triglyceride | (3) | 9.00 |
| | Stearic acid | Stearic Acid | (1) | 3.00 |
| | Antaron V-216 | PVP/Hexadecene Copolymer | (4) | 2.00 |
| | Oxynex ® K liquid | Tocopherol, Ascorbyl Palmitate, Ascorbic Acid, Citric Acid, PEG-8 | (1) | 0.10 |
| | Preservative | Propylparaben | | q.s. |

Preparation:

Heat phase B at about 80° C. until everything has melted, and cool to 65° C. The constituents of phase A are then added with stirring, and the finished eye shadow is packed while still liquid.

Sources of Supply:
(1) Merck KGaA
(2) Croda
(3) Hüls AG
(4) ISP Europe

Example 7

Nail varnish

| Ingredient | Composition | Manufacturer | % |
|---|---|---|---|
| Nail varnish base 2702 | Nitrocellulose base | (2) | 89.75 |
| Timiron ® Splendid Green | TiO$_2$/SiO$_2$ mica pigment having a particle size of 10–60 µm | (1) | 2.00 |
| Nailsyn ® Sterling 60 | BiOCl in nitrocellulose | (1) | 5.00 |
| Yellow HO 203 | FD&C Yellow No. 5 in nitrocellulose base | (2) | 0.90 |
| Blue HO 208 | Berlin Blue in nitrocellulose | (2) | 0.35 |
| White HO 1270 | TiO$_2$ in nitrocellulose | (2) | 2.00 |

Preparation:

The BiOCl dispersion and the pigments are added successively to the nail-varnish base with stirring. The mixture is subsequently stirred at 1000 rpm for a further 10 minutes.

Sources of Supply:
(1) Merck KGaA
(2) International Lacquers

Example 8

Eye shadow

| Phase | Ingredient | Composition | Manufacturer | % |
|---|---|---|---|---|
| A | | Fe$_2$O$_3$-coated BiOCl pigment having a particle size of 2–35 µm | (1) | 3.50 |
| | Ronasphere ® | Silica | (1) | 5.00 |
| | Magnesium stearate | Magnesium Stearate | (1) | 2.50 |
| | White clay | Kaolin | (1) | 5.00 |
| | Hubersorb 600 | Calcium Silicate | (2) | 0.50 |
| | Talcum | Talc | (1) | 15.80 |
| B | Corona ® Magenta | TiO$_2$/mica pigment + CI 75470 (carmine) having a particle size of 10–60 µm | (1) | 55.00 |
| C | Amerchol L-101 | Mineral oil, Lanolin, Alcohol | (3) | 10.70 |
| | Super Hartolan | Lanolin alcohol | (4) | 1.00 |
| | Ewalin 1751 | Petrolatum | (5) | 1.00 |
| | Preservative | | | q.s. |
| | Perfume oil | | | q.s. |

Preparation:

Combine the constituents of phase A and sieve through 63 µm. Subsequently add phase B, and add the molten phase C dropwise to the powder mixture with vigorous stirring. The powders are pressed at 40–50 bar.

Sources of Supply:
(1) Merck KGaA
(2) Huber
(3) Amerchol
(4) Croda
(5) H. E. Wagner

Example 9

Lip powder comprising 30% of pearlescent pigment and 10% of Biron ® fines

| Phase | Ingredient | Composition | Manufacturer | % |
|---|---|---|---|---|
| A | Bicrona ® Carmine | Carmine Red-coated BiOCl pigment having a particle size of 2–20 µm | (1) | 40.0 |
|  | Talcum | Talc | (1) | 30.0 |
|  | Ronasphere ® LDP | Silica with TiO$_2$/Fe$_2$O$_3$ coating |  | 10.0 |
|  | Magnesium stearate | Magnesium Stearate | (1) | 5.0 |
| B | Isopropyl stearate | Isopropyl Stearate | (2) | 11.2 |
|  | Dow Corning 1403 fluid | Dimethicone, Dimethiconol | (3) | 3.8 |
|  | Perfume oil |  |  | q.s. |
|  | Preservative | Propylparaben |  | q.s. |

Preparation:

Combine and pre-mix the constituents of phase A. Subsequently add the molten phase B dropwise to the powder mixture with stirring. The powders are pressed at 40–50 bar.

Sources of Supply:
(1) Merck KGaA
(2) Henkel KGaA
(3) Dow Corning

Example 10

Powder compact

| Phase | Ingredient | Composition | Manufacturer | % |
|---|---|---|---|---|
| A | Microna ® Matte White | TiO$_2$/ZnO mica pigment having a particle size of 2–15 µm | (1) | 18.6 |
|  | Microna ® Matte Orange | Fe$_2$O$_3$ mica pigment having a particle size of <15 µm | (1) | 3.8 |
|  | Microna ® Matte Yellow | FeOOH mica pigment having a particle size of <15 µm | (1) | 3.8 |
|  | Microna ® Matte Black | Fe$_3$O$_4$ mica pigment having a particle size of <15 µm | (1) | 3.8 |
|  | Biron ® ESQ | BiOCl pigment | (1) | 10.0 |
|  | Satin Mica | Mica | (1) | to 100% |
|  | Orgasol 2002 | Nylon-12 | (2) | 6.0 |
|  | Talcum | Talc | (1) | 10.0 |
|  | Ronasphere ® LDP | Silica with TiO$_2$/Fe$_2$O$_3$ coating | (1) | 10.0 |
| B | Hest CSO | Cetearyl Octanoate | (3) | 1.0 |
|  | Ivarlan 3350 | Isopropyl Lanolate | (4) | 1.5 |
|  | Crodamol OP | Octylpalmitate | (5) | 3.0 |
|  | Perfume oil | Perfume |  | q.s. |
|  | Preservative |  |  | q.s. |

Preparation:

Combine, pre-mix and sieve (100 µm) the constituents of phase A. Subsequently stir phase B dropwise into the dissolved binder until a homogeneous distribution has been achieved. Subsequently pack and press.

Sources of Supply:
(1) Merck KGaA
(2) Elf Atochem
(3) Heterene
(4) Brooks
(5) Croda

Example 11

Two way cake make-up

| Phase | Ingredient | Composition | Manufacturer | % |
|---|---|---|---|---|
| A | Microna ® Matte White | TiO$_2$/ZnO mica pigment having a particle size of 2–15 µm | (1) | 18.6 |
|  | Microna ® Matte Orange | Fe$_2$O$_3$ mica pigment having a particle size of <15 µm | (1) | 3.8 |
|  | Microna ® Matte Yellow | FeOOH mica pigment having a particle size of <15 µm | (1) | 3.8 |
|  | Microna ® Matte Black | Fe$_3$O$_4$ mica pigment having a particle size of <15 µm | (1) | 3.8 |
|  | Biron ® MTU | BiOCl pigment | (1) | 10.0 |
|  | Satin Mica | Mica | (1) | to 100% |
|  | Orgasol 2002 | Nylon-12 | (2) | 6.0 |
|  | Talcum | Talc | (1) | 20.0 |
|  | Ronasphere ® LDP | Silica with TiO$_2$/Fe$_2$O$_3$ coating | (1) | 10.0 |
| B |  | Hydrogenated Castor Oil | (3) | 2.0 |
|  |  | Propylene glycol Caprilate | (4) | 5.0 |
|  |  | Sorbitan Oleate (P.OE)20 | (5) | 0.1 |
|  | Crill 3 | Sorbitan Stearate | (5) | 0.1 |
|  | Perfume oil | Perfume |  | 0.5 |
|  | Preservative |  |  | 0.2 |

Preparation:

Combine, pre-mix and sieve (100 µm) the constituents of phase A. Mix the constituents of phase B and heat until everything has dissolved. Add phase B to phase A until a homogeneous distribution has occurred, and pack.

Sources of Supply:
(1) Merck KGaA
(2) Elf Atochem
(3) Cognis
(4) Nikko
(5) Croda

What is claimed is:

1. A pigment mixture in the form of a dispersion, comprising at least two components, a component A comprising coated or uncoated BiOCl pigment, and a component B comprising a pearlescent pigment comprising mica, Fe$_2$O$_3$, glass, TiO$_2$, SiO$_2$, polymer or graphite platelets, or platelet-shaped, needle-shaped or spherical colorants and/or fillers.

2. The pigment mixture according to claim 1 wherein component A comprises BiOCl pigments which have been coated with Fe$_2$O$_3$, Canine Red, Berlin Blue or chromium oxide green.

3. The pigment mixture according to claim 1, wherein the pearlescent pigment is a multilayered pigment.

4. The pigment mixture according to claim 3, wherein component B comprises a multilayered pigment which has an Fe$_2$O$_3$ coating, a TiO$_2$/Fe$_2$O$_3$, SiO$_2$, TiO$_2$/Fe$_2$O$_3$ coating or a TiO$_2$, SiO$_2$, TiO$_2$ coating.

5. The pigment mixture according to claim 1, wherein component B comprises organic and/or inorganic dyes of synthetic or natural origin, coated mica platelets, spherical SiO$_2$, coated or uncoated, carbon black, organic colored pigments and/or inorganic colored pigments.

6. The pigment mixture according to claim 1, wherein the BiOCl pigment is in the form of a nitrocellulose or castor oil dispersion.

7. The pigment mixture according to claim 1, wherein component A and component B are mixed in a ratio of from 90:1 to 1:90.

8. The pigment mixture according to claim 1 additionally comprising a UV stabilizer.

9. A formulation comprising a pigment mixture according to claim 1, wherein the formulation is a paint, coating, printing ink, plastic, powder coating, plastic film, or cosmetic formulation.

10. The pigment mixture according to claim 1, wherein component A and component B are mixed in a ratio of from 50:1 to 1:50.

11. The pigment mixture according to claim 1, wherein component A and component B are mixed in a ratio of from 20:1 to 1:20.

12. The pigment mixture according to claim 1, wherein the BiOCl pigment is in the form of particles of 1–100 μm size.

13. The pigment mixture according to claim 1, wherein the BiOCl pigment is in the form of particles of 2–35 μm size.

14. The pigment mixture according to claim 1, wherein the BiOCl pigment has a coating comprising a metal oxide or an organic or inorganic colorant.

15. The pigment mixture according to claim 1, wherein the BiOCl pigment has a coating comprising $TiO_2$, a $TiO_2$ suboxide or $Fe_2O_3$.

* * * * *

UNITED STATES PATENT AND TRADEMARK OFFICE
CERTIFICATE OF CORRECTION

PATENT NO.    : 6,743,285 B1
DATED         : June 1, 2004
INVENTOR(S)   : Ralf Anselmann et al.

It is certified that error appears in the above-identified patent and that said Letters Patent is hereby corrected as shown below:

Column 12,
Line 52, reads "canine" should read -- carmine --

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,743,285 B1 | Page 1 of 1 |
| APPLICATION NO. | : 10/069669 | |
| DATED | : June 1, 2004 | |
| INVENTOR(S) | : Anselmann et al. | |

It is certified that error appears in the above-identified patent and that said Letters Patent is hereby corrected as shown below:

On the Title Page

Item (30) "Foreign Application Priority Data" reads "Sep. 1, 2000 (DE) 199 41 607" should read -- Sep. 1, 1999 (DE) 199 41 607 --

Signed and Sealed this
Sixteenth Day of December, 2014

Michelle K. Lee
*Deputy Director of the United States Patent and Trademark Office*